(12) United States Patent
Yazdanfar et al.

(10) Patent No.: US 10,531,862 B2
(45) Date of Patent: Jan. 14, 2020

(54) SYSTEM AND METHOD FOR ATTACHING A BIOPSY COLLECTING DEVICE TO A SPECTROSCOPY SYSTEM

(71) Applicant: General Electric Company, Schenectady, NY (US)

(72) Inventors: Siavash Yazdanfar, Niskayuna, NY (US); Victor Petrovich Ostroverkhov, Ballston Lake, NY (US); Dmitry Vladimirovich Dylov, Niskayuna, NY (US); Stephen B. Solomon, New York, NY (US); Jeremy C. Durack, New York, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 268 days.

(21) Appl. No.: 14/657,085

(22) Filed: Mar. 13, 2015

(65) Prior Publication Data
US 2015/0182204 A1    Jul. 2, 2015

Related U.S. Application Data

(63) Continuation-in-part of application No. 13/927,807, filed on Jun. 26, 2013, now abandoned.

(51) Int. Cl.
*A61B 10/02* (2006.01)
*G01N 1/31* (2006.01)

(52) U.S. Cl.
CPC ...... *A61B 10/0233* (2013.01); *A61B 10/0275* (2013.01); *A61B 2010/0208* (2013.01); *A61B 2560/0456* (2013.01); *G01N 1/31* (2013.01)

(58) Field of Classification Search
CPC ........ G01J 3/0256; G01J 3/027; G01J 3/0291; G01J 2003/062; A61B 2560/0456; A61B 2010/0208; A61B 10/0233–0283
See application file for complete search history.

(56) References Cited

U.S. PATENT DOCUMENTS

| 5,612,540 | A | 3/1997 | Richards-Kortum et al. |
| 6,174,291 | B1 | 1/2001 | McMohan et al. |
| 6,258,576 | B1 | 7/2001 | Richards-Kortum et al. |
| 8,517,985 | B2 * | 8/2013 | Wei ........................ A61M 5/46 604/117 |

(Continued)

FOREIGN PATENT DOCUMENTS

| WO | 2005122878 A1 | 12/2005 |
| WO | 2014063257 A1 | 5/2014 |

OTHER PUBLICATIONS

Ramanujam, "Fluorescence Spectroscopy of Neoplastic and Non-Neoplastic Tissues", Neoplasia, vol. 2, Issue 1-2, pp. 89-117, Jan.-Apr. 2000.

(Continued)

*Primary Examiner* — Devin B Henson
*Assistant Examiner* — Huong Q. Nguyen
(74) *Attorney, Agent, or Firm* — Fletcher Yoder, P.C.

(57) ABSTRACT

A biopsy collecting device includes a needle unit comprising a biopsy specimen. Also, the biopsy collecting device includes an activator unit operatively coupled to the needle unit and including a channel at a bottom surface of the activator unit, wherein the channel is configured to detachably couple the biopsy collecting device to an attaching unit of a spectroscopy system.

12 Claims, 9 Drawing Sheets

(56) References Cited

U.S. PATENT DOCUMENTS

| | | | |
|---|---|---|---|
| 2004/0077972 A1* | 4/2004 | Tsonton | A61B 10/0275 600/564 |
| 2006/0189860 A1 | 8/2006 | Hacker et al. | |
| 2008/0034833 A1* | 2/2008 | Maier | G01J 3/02 73/1.01 |
| 2008/0194969 A1 | 8/2008 | Werahera et al. | |
| 2009/0270725 A1* | 10/2009 | Leimbach | A61B 10/0275 600/431 |
| 2010/0301229 A1 | 12/2010 | Ramanujam et al. | |
| 2012/0075619 A1 | 3/2012 | Nieman et al. | |
| 2012/0184827 A1* | 7/2012 | Shwartz | A61B 5/0075 600/302 |
| 2012/0265051 A1* | 10/2012 | Fischer | A61B 10/0241 600/411 |
| 2013/0108138 A1* | 5/2013 | Nakayama | A61B 6/022 382/132 |

OTHER PUBLICATIONS

Drezek et al., "Light scattering from cervical cells throughout neoplastic progression: influence of nuclear morphology, DNA content, and chromatin texture", Journal of Biomedical Optics, vol. 8, Issue 1, pp. 7-16, Jan. 1, 2003.

Zhu et al., "Diagnosis of breast cancer using fluorescence and diffuse reflectance spectroscopy: a Monte-Carlo model-based approach", Journal of Biomedical Optics, vol. 13, Issue 3, pp. 034015, May-Jun. 2008.

Balachandran et al., "Cytology workforce study: a report of current practices and trends in New York State", American Journal of Clinical Pathology, vol. 136, pp. 108-118, 2011.

Office Action for U.S. Appl. No. 14/657,204 dated Jan. 23, 2017; 16 Pages.

* cited by examiner

SYSTEM AND METHOD FOR ATTACHING A BIOPSY COLLECTING DEVICE TO A SPECTROSCOPY SYSTEM

CROSS-REFERENCE TO RELATED APPLICATIONS

This application is a continuation in part of U.S. patent application Ser. No. 13/927,807, entitled "System and Method for Holding a Biopsy Collecting Device", filed 26 Jun. 2013, which is herein incorporated by reference. This application is also related to U.S. patent application entitled "System and Method for Tissue Classification" filed concurrently herewith under U.S. patent application Ser. No. 14/657,204 and which issued as U.S. Pat. No. 9,913,628, the entire disclosure is incorporated herein by reference.

BACKGROUND

Embodiments of the present disclosure relate generally to optical spectroscopy, and more particularly to a system and a method for quantifying an amount of diagnostic tissue and determining types of tissues within the excised biopsy specimen using optical spectroscopy.

In many fields of medicine, tissue classification is widely used to aid diagnosis in a patient. For example, when a patient presents with a suspicious deep tissue lesion, such as those identified during a diagnostic CT scan, the typical workup includes tissue classification to assist in diagnosis and stratify patients for further testing.

Among the existing techniques, core needle biopsy (CNB) is increasingly used as a minimally invasive method to acquire a representative sample of a deep tissue lesion. Typically in CNB, needle intervention is used for taking tissue biopsies and submitting it to pathology to determine a diagnosis. Compared to surgical or excisional biopsy, CNB procedure is less invasive, less expensive, faster, minimizes deformity, leaves little or no scarring and requires a shorter time for recovery. Also, CNB may obviate the need for surgery in a patient with benign lesions and also reduce the number of surgical procedures performed in the patient.

In general, the CNB is a common procedure used to obtain a biopsy specimen that includes a physical sample of a tissue site. Further, the biopsy specimen may be analyzed in a pathology laboratory using histopathological techniques to determine whether the tissue sample is cancerous. However, one of the problems in CNB is that approximately 15-20% of biopsy specimens/samples are non-diagnostic, which yields too little tissue for a definitive diagnosis. As a result, in some cases, the CNB procedure may be repeated to obtain a viable amount of biopsy specimen/sample from the patient, which may create further complications to the patient. For example, piercing the needle repeatedly into lungs to obtain the biopsy specimen may result in a collapsed lung.

Moreover, the amount of diagnostic tissue in the biopsy specimen may limit the number and types of tests available to the pathologist several days following the biopsy procedure, potentially resulting in a delayed diagnosis and increased risk to the patient. Since the advent of new molecular pathology tests requires a larger amount of viable cancer tissue than conventional histopathology, this problem is likely to increase. Thus, there is a need for an improved method and system for quantifying the amount of diagnostic tissue and determining types of tissues within the excised biopsy specimen.

BRIEF DESCRIPTION

In accordance with one embodiment described herein, a biopsy collecting device includes a needle unit comprising a biopsy specimen. Also, the biopsy collecting device includes an activator unit operatively coupled to the needle unit and comprising a channel at a bottom surface of the activator unit, wherein the channel is configured to detachably couple the biopsy collecting device to an attaching unit of a spectroscopy system.

In accordance with a further aspect of the present disclosure, a method for holding a biopsy collecting device includes collecting, by a needle unit, a biopsy specimen from a patient. Also, the method includes detachably coupling a female stepped-groove of an activator unit with a male stepped-groove of an attaching unit of a spectroscopy system so as to couple the biopsy collecting device to the attaching unit of a spectroscopy system.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As will be described in detail hereinafter, various embodiments of exemplary structures and methods for diagnosing tissue are presented. By employing the methods and the various embodiments of the system described hereinafter, the amount of diagnostic tissue and types of tissues in an excised biopsy specimen is determined without removing the biopsy specimen from the biopsy needle or the biopsy collecting device.

Figure 1:
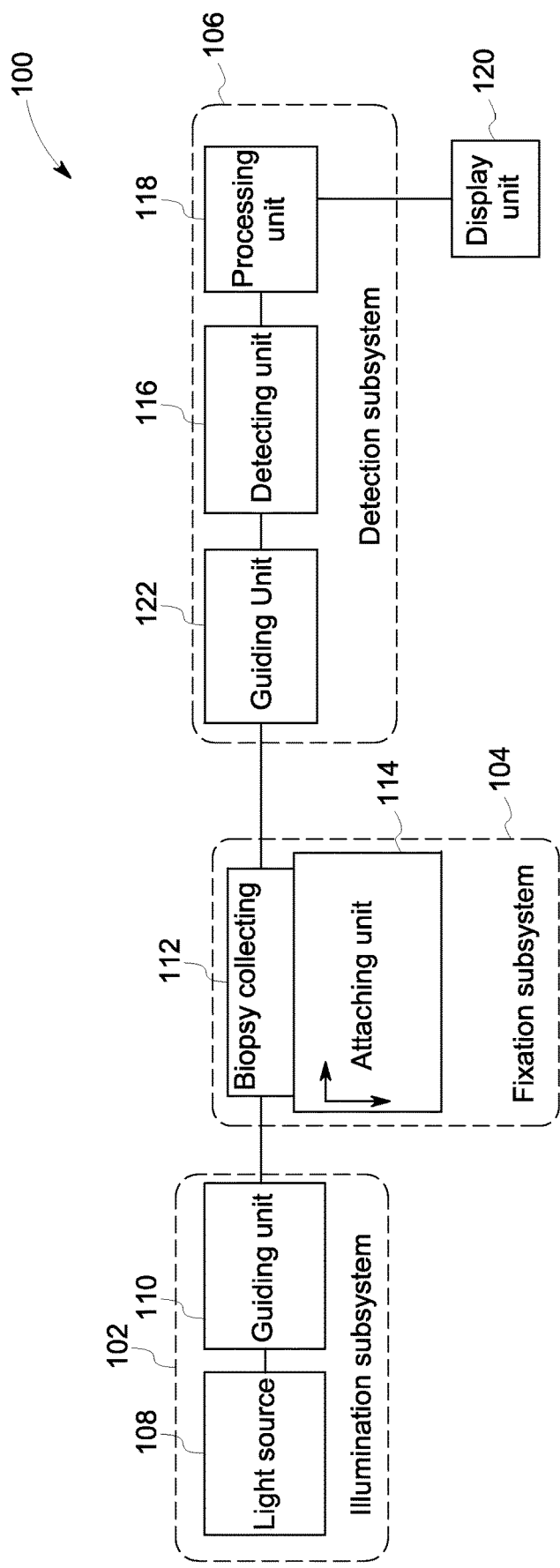
FIG. 1 is a block diagram of a spectroscopy system for diagnosing tissue in a biopsy specimen, in accordance with aspects of the present disclosure.

Turning now to the drawings, and referring to FIG. 1, a spectroscopy system for diagnosing tissue, in accordance with aspects of the present disclosure, is depicted. The spectroscopy system 100 may be used to determine an amount of diagnostic tissue and types of tissues present in an excised biopsy specimen. More specifically, the biopsy specimen may include one or more tissue samples that are classified into one or more tissue classes, which in turn aids in determining a quantity and/or a quality of the diagnostic tissue in the biopsy specimen. In one example, the one or more tissue classes may include a normal tissue class and an abnormal tissue class. The normal tissue class is referred to as a class of tissue samples having no cancerous tissues, such as benign tissue or blood, while the abnormal tissue class is referred to as a class of tissue samples having cancerous tissues, including malignant or necrotic tumor, or other diseased tissue such as fibrosis. Also, the spectroscopy system 100 may be used to characterize the biopsy specimen in a biopsy needle or a biopsy collecting device immediately after excision. It is to be noted that the biopsy specimen may be referred to as a physical sample of a region in a patient. In one example, the biopsy specimen may include at least a normal tissue and/or a cancerous tissue of a patient.

In accordance with one embodiment, the spectroscopy system 100 includes an illumination subsystem 102, a fixation subsystem 104, and a detection subsystem 106. The illumination subsystem 102 is configured to emit an illumination light towards the biopsy specimen. The illumination light may be in a range from about 200 nm to about 1100 nm. As depicted in FIG. 1, the illumination subsystem 102 includes a light source 108 and a guiding unit 110 that is coupled to the light source 108. In one example, the light source 108 may include a deuterium tungsten halogen source that is configured to emit a broadband light or a narrowband light towards the biopsy specimen. Further, the guiding unit 110 may include optical fibers and lenses that are used for guiding the emitted illumination light towards the biopsy specimen. In one embodiment, the guiding unit 110 may include a plurality of optical fibers that are used to deliver the emitted illumination light at multiple locations along the biopsy specimen.

In a presently contemplated configuration, the fixation subsystem 104 is configured to position the biopsy specimen across the illumination light that is emitted by the illumination subsystem 102. As depicted in FIG. 1, the fixation subsystem 104 includes an attaching unit 114 that is configured to hold a biopsy collecting device 112 having the biopsy specimen. Particularly, the biopsy collecting device 112 may include an activator unit and a needle unit. A portion of the needle unit may be pierced into the patient towards a sample/tissue site to obtain the biopsy specimen. Thereafter, the biopsy collecting device 112 may be fastened to the attaching unit 114 that provides an interface between the biopsy collecting device 112 and the detection subsystem 106.

In addition, the attaching unit 114 is used for positioning the biopsy collecting device 112 at a predetermined position and/or angle in the spectroscopy system 100 so that the illumination light may scan the biopsy specimen present in the needle unit. More specifically, the attaching unit 114 may be used for precisely positioning at least the needle unit relative to the illumination light while scanning the biopsy specimen. In one example, the attaching unit 114 may include one or more actuators that are employed for moving the biopsy collecting device 112 in a forward or backward direction with respect to an illumination path. The aspect of positioning the biopsy specimen across the illumination light is explained in greater detail with reference to FIG. 6.

Furthermore, the detection subsystem 106 is coupled to the fixation subsystem 104 and aligned with the illumination subsystem 102 for determining the diagnostic tissue in the biopsy specimen. The detection modality may be based on a variety of optical detection methods including but not limited to, diffuse optical spectroscopy, fluorescence spectroscopy, optical coherence tomography, Raman spectroscopy, or combinations thereof. In one exemplary embodiment, the detection subsystem uses diffuse optical spectroscopy for determining the diagnostic tissue in the biopsy specimen.

As depicted in FIG. 1, the detection subsystem 106 includes a guiding unit 122, a detecting unit 116, and a processing unit 118. The guiding unit 122 may include optical fibers and lenses that are used for guiding the light comprising an attenuated illumination light and/or a re-emitted light from the biopsy specimen. In one embodiment, the guiding unit 122 may include a plurality of optical fibers that are used to guide the attenuated illumination light and/or the re-emitted light towards the detecting unit 116. Further, the detecting unit 116 is used for generating an electrical signal corresponding to the attenuated illumination light and/or the re-emitted light from the biopsy specimen. Particularly, the detecting unit 116 includes one or more optical detectors that are aligned with the illumination path so as to receive the illumination light emitted by the illumination subsystem 102 and the light re-emitted from the biopsy specimen via the guiding unit 122. The received light may be attenuated by one or more molecules in the biopsy specimen. More specifically, the molecules in the biopsy specimen may absorb, scatter, and/or attenuate the illumination light while passing through the biopsy specimen. This in turn causes transmission losses at various wavelengths in spectra of the illumination light. It is to be noted that the illumination light with such transmission losses may also be referred to as the attenuated illumination light. In one embodiment, the received light may be comprised of attenuated illumination light with transmission losses at various wavelengths, which may include information on the absorbance of molecules comprising the tissue, the inhomogeneity of the tissue refractive index, and the secondary light re-emitted by molecules due to fluorescence and/or Raman scattering phenomena. Also, it may be noted that the received and emitted illumination light paths may be in more than one direction. In one example, the illumination path may be orthogonal or at an oblique angle, e.g., 45 degrees, to the detected light path. Further, the detected light is converted to a corresponding electrical signal.

In addition, the processing unit 118 that is coupled to the detecting unit 116 may receive the electrical signal representing the received light. Further, the received electrical signal is processed to determine the diagnostic tissue in the biopsy specimen. Particularly, the spectrum of the received light may be analyzed to classify tissues into one or more tissue types, which in turn used to classify the tissue sample into at least one of the normal tissue class and the abnormal tissue class. Thereafter, the classified tissue sample is used to determine the quantity and the quality of the diagnostic tissue in the biopsy specimen. Also, the processing unit 118 may display the classified tissue types and the tissue sample in one or more forms on a display unit 120 that is coupled to the processing unit 118. The aspect of processing the spectrum of the received light and displaying the classified tissue types is explained in greater detail with reference to FIG. 7.

After completion of the analysis, the biopsy specimen may be removed from the biopsy collecting device and transferred to a tissue fixation medium, e.g., formalin, for pathology. Thus, by using the exemplary spectroscopy system 100, the diagnostic tissue within the excised biopsy specimen is determined without removing the biopsy specimen from the biopsy needle or the biopsy collecting device. Also, conducting analysis directly in the biopsy needle or the biopsy collecting device may minimize stress on the biopsy specimen/sample and impact on workflow, prior to transferring the biopsy specimen/sample for histopathology or cytopathology. In one embodiment, the biopsy collecting device may include a tissue collecting chamber or a tissue container that is used for collecting the tissue from the biopsy needle. Further, this tissue may be positioned across the illumination path of the spectroscopy system for further analysis, classification, and/or quantification of the tissue.

Figure 2:
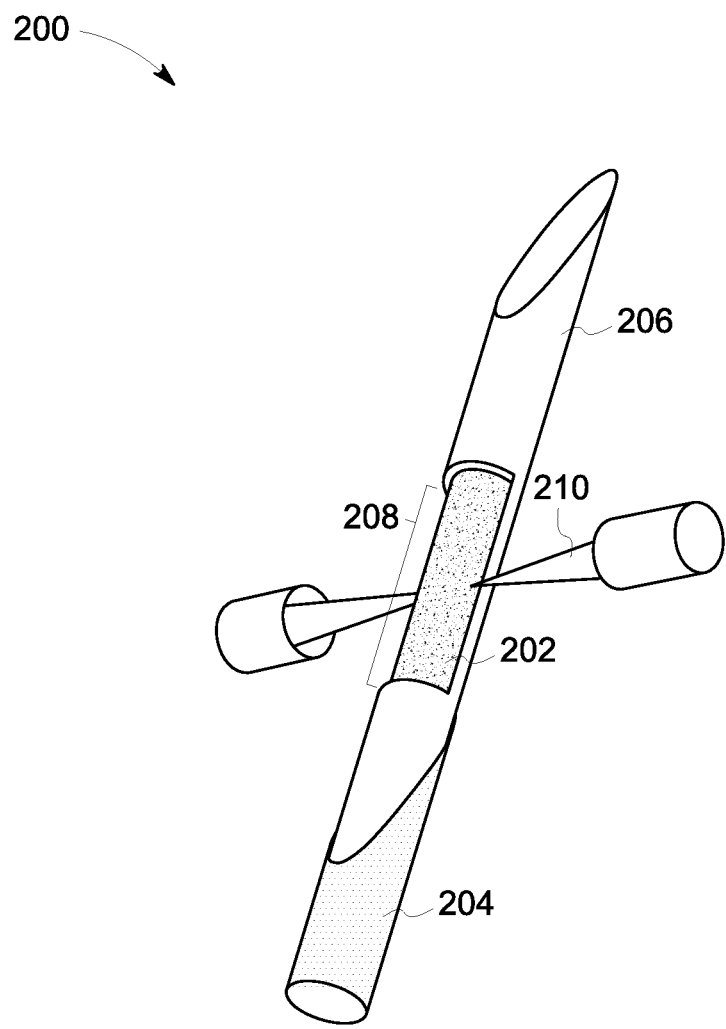
FIG. 2 is an illustration of a needle unit comprising a biopsy specimen, in accordance with aspects of the present disclosure.

Referring to FIG. 2, an illustration of a needle unit comprising a biopsy specimen, in accordance with aspects of the present disclosure, is depicted. For ease of understanding, the needle unit 200 is described with reference to the components of FIG. 1. It is to be noted that the needle unit 200 may be considered as a part or a component of the biopsy collecting device. As appreciated, the needle unit 200 may be pierced into a patient towards a desired tissue or sample site to obtain the biopsy specimen 202 from the patient. As depicted in FIG. 2, the needle unit 200 includes an outer sheath, which is known as a cannula 204 and an inner sheath, which is known as a stylet 206. The stylet 206 may be configured to extend or retract from the cannula 204. Further, the stylet 206 may have a collection area 208 for collecting the biopsy specimen 202 from the patient.

Moreover, upon collecting the biopsy specimen 202 from the patient, the biopsy collecting device having the needle unit 200 may be fastened to the attaching unit 114. In one embodiment, the stylet 206 may be extended or retracted to position the biopsy specimen 202 across an illumination path 210. Also, in another embodiment, the stylet 206 may be extended or retracted so that the illumination light may scan the biopsy specimen 202 at multiple locations. The aspect of fastening the needle unit 200 and scanning the biopsy specimen 202 is explained in greater detail with reference to FIG. 4.

Figure 3:
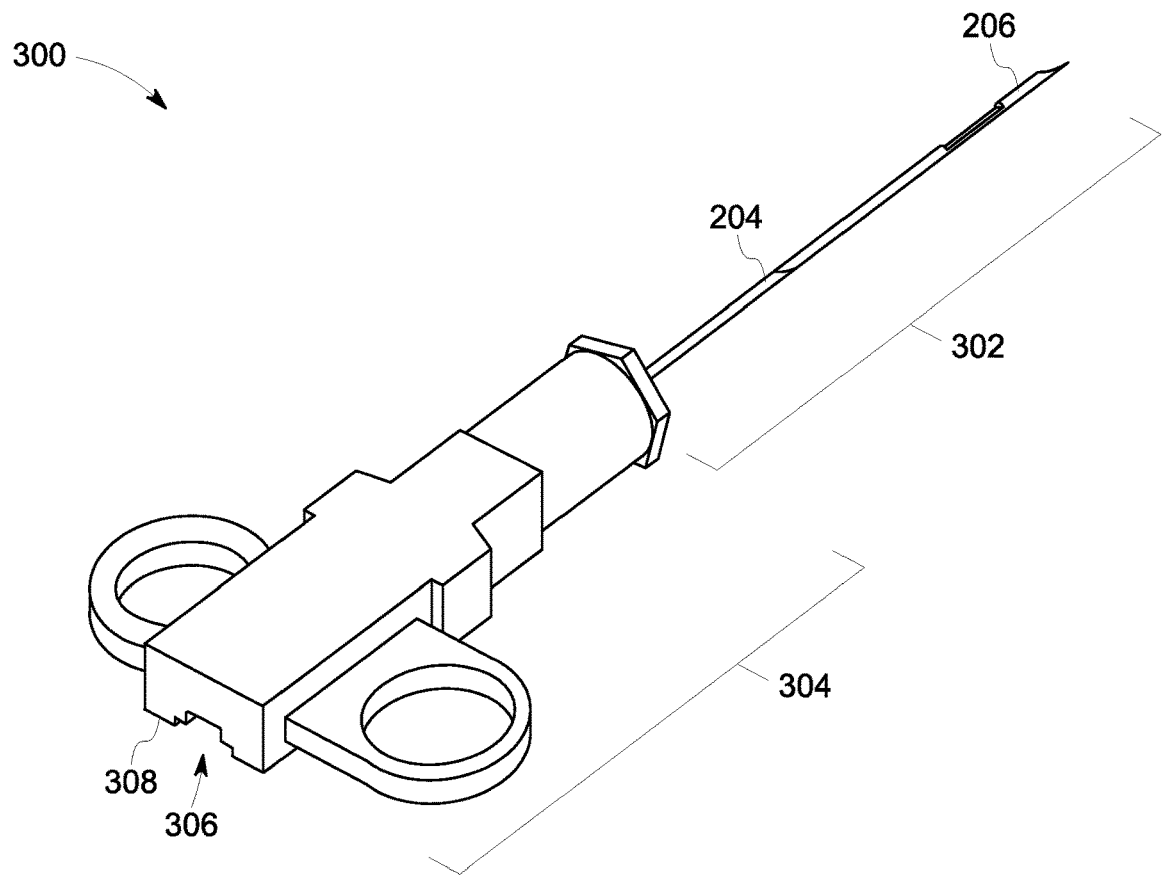
FIG. 3 is a diagrammatical representation of a top view of a biopsy collecting device, in accordance with aspects of the present disclosure.
Figure 4:
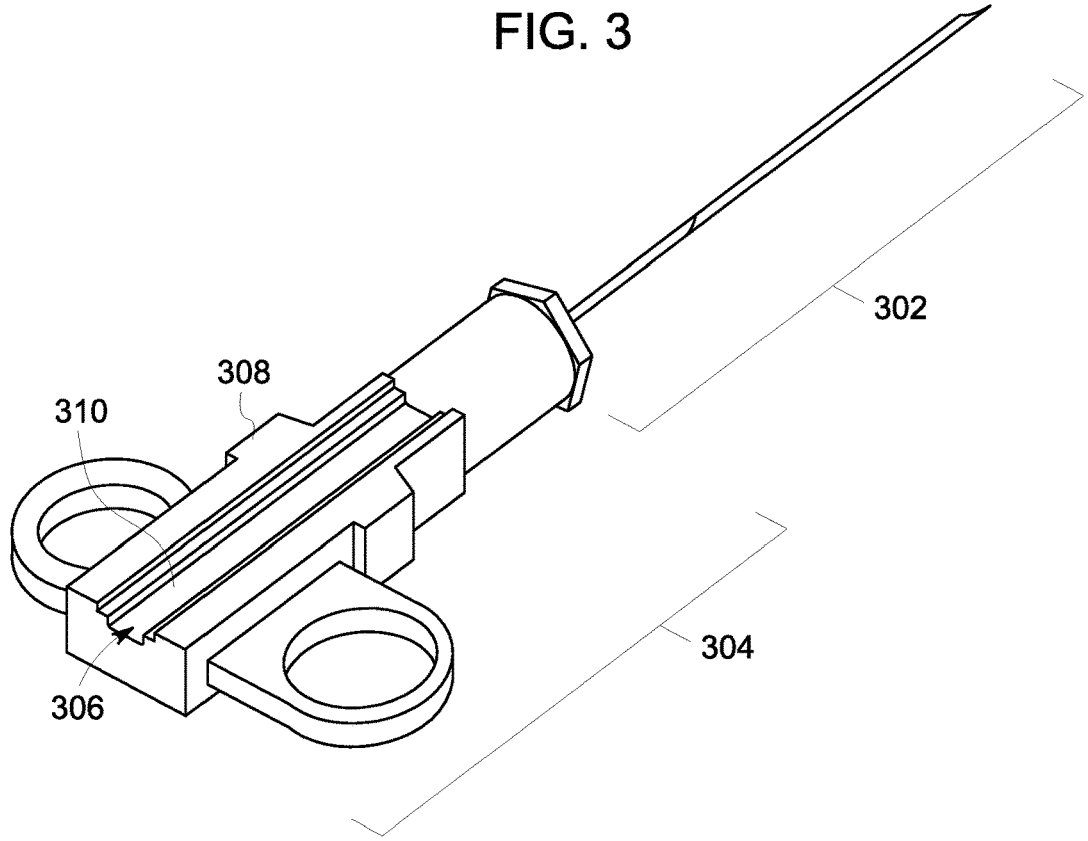
FIG. 4 is a diagrammatical representation of a bottom view of the biopsy collecting device, in accordance with aspects of the present disclosure.

FIG. 3 is a diagrammatical representation of a top view of a biopsy collecting device, in accordance with aspects of the present disclosure. Also, FIG. 4 is a diagrammatical representation of a bottom view of the biopsy collecting device, in accordance with aspects of the present disclosure. Reference numeral 300 may be representative of the biopsy collecting device 112 of FIG. 1. The biopsy collecting device 300 includes a needle unit 302 and an activator unit 304. The needle unit 302 may be similar to the needle unit 200 of FIG. 2. The activator unit 304 is coupled to a rear end of the needle unit 302 and is configured to extend or retract the stylet 206 relative to the cannula 204.

Further, the activator unit 304 includes a channel 306 at a bottom surface 308 of the activator unit 304. The channel 304 is configured to detachably couple the biopsy collecting device 300 to the attaching unit 114 of the spectroscopy system 100. Particularly, the channel 306 includes a female stepped-groove 310 on the bottom surface 308 of the activator unit 304. In one example, the female stepped-groove 310 is along a length of the activator unit 304. Also, the female stepped-groove 310 matches with a male stepped-groove (see FIG. 5) of the attaching unit 114. In one embodiment, the female stepped-groove 310 may be coupled to the male stepped-groove of the attaching unit 114 to form a track area for the biopsy collecting device 300 to move laterally or along the axis of the needle unit 302 on the spectroscopy system 100. In one embodiment, the activator unit 304 may include the male stepped-groove at the bottom surface 308 of the activator unit 304, and the attaching unit 114 may include the female stepped-groove at the top surface of the attaching unit 114. Further, the male stepped-groove of the activator unit 304 may be coupled to the female stepped-groove of the attaching unit 114 to form a track area for the biopsy collecting device 300 to move along the axis of the needle unit 302 on the spectroscopy system 100. It may be noted that the activator unit 304 may be coupled to the spectroscopy system 100 by employing other coupling mechanism, and is not limited to the male-female groove coupling as depicted in FIGS. 3 and 4.

In one embodiment, the activator unit 304 may be magnetically coupled to the spectroscopy system 100. Particularly, the bottom surface of the activator unit 304 and the top surface of the spectroscopy system 100 may include magnetic material. Further, when the activator unit 304 is placed on the spectroscopy system 100, the bottom surface of the activator unit 304 may magnetically couple with the top surface of the spectroscopy system 100.

Figure 5:
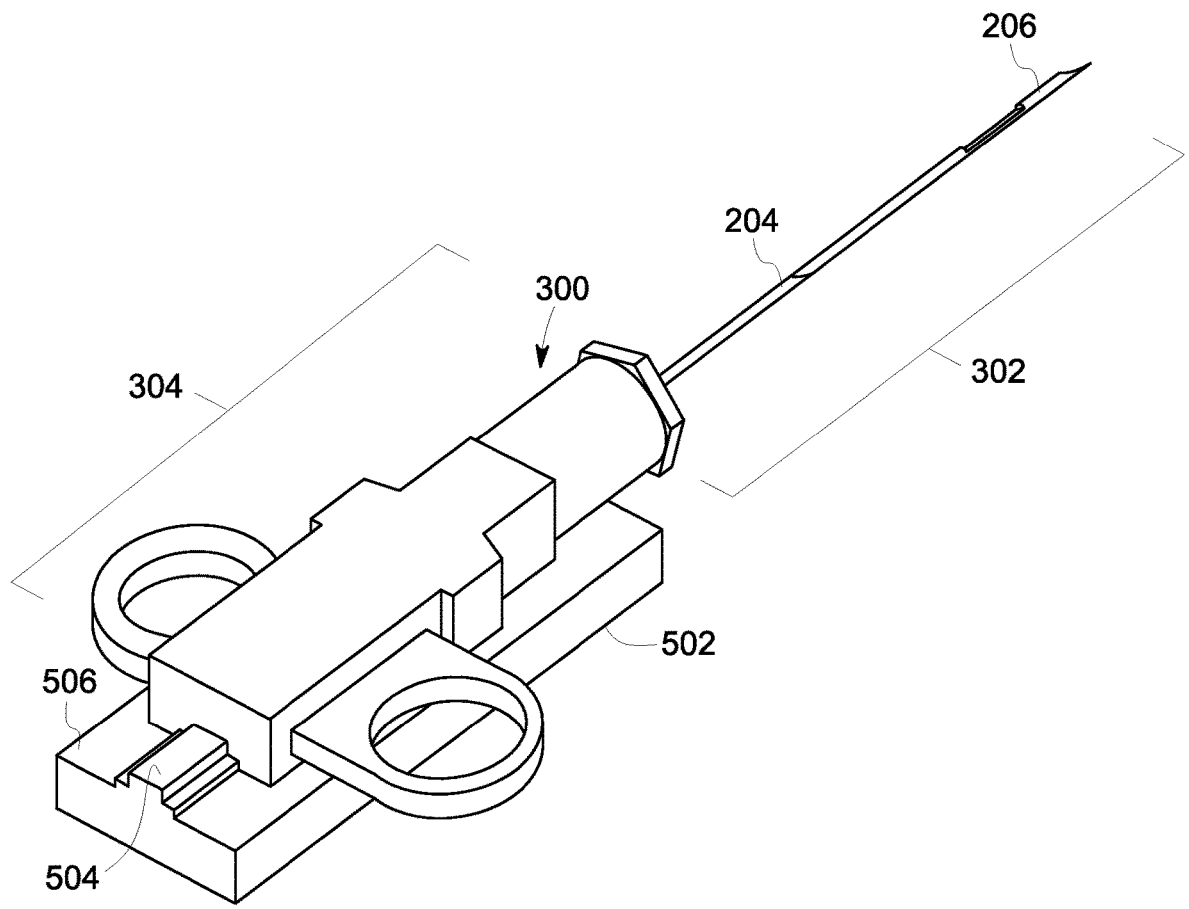
FIG. 5 is an illustration of an attaching unit holding the biopsy collecting device, in accordance with aspects of the present disclosure.

Referring to FIG. 5, an attaching unit having a biopsy collecting device, in accordance with aspects of the present disclosure is depicted. Reference numeral 502 may be representative of the attaching unit 114 of FIG. 1. The biopsy collecting 300 device is used to obtain a biopsy specimen from a patient, and then it is coupled to the attaching unit 502. As depicted in FIG. 5, the biopsy collecting device 300 includes an activator unit 304 and a needle unit 302. The needle unit 302 is representative of the needle unit 200 of FIG. 2.

In a presently contemplated configuration, the attaching unit 502 is configured to fasten the activator unit 304 of the biopsy collecting device 300 to the spectroscopy system 100. Particularly, the attaching unit 502 includes a male stepped-groove 504 on a top surface 506 of the attaching unit 502. The male stepped-groove 504 is along a length of the attaching unit 502. Also, the male stepped-groove 504 matches with the female stepped-groove 310 of the biopsy collecting device 300. Particularly, the female stepped-groove 310 of the biopsy collecting device 300 may be slidably coupled to the male stepped-groove 504 of the spectroscopy system 100 to allow lateral movement of the biopsy collecting device 300 on the attaching unit 502. In one embodiment, the activator unit 304 slides over the attaching unit 502 to align the needle unit 302 at a predetermined position and/or angle on the spectroscopy system 100.

In an alternate embodiment, the biopsy collecting device 300 may be interfaced to the attaching unit 502. Particularly, the activator unit 304 may include a tab that snaps into the attaching unit 502 directly. It may be noted that the biopsy collecting device 300 may be coupled to the attaching unit 502 by using any fastening structure, and is not limited to the structure shown in FIG. 5.

Figure 6:
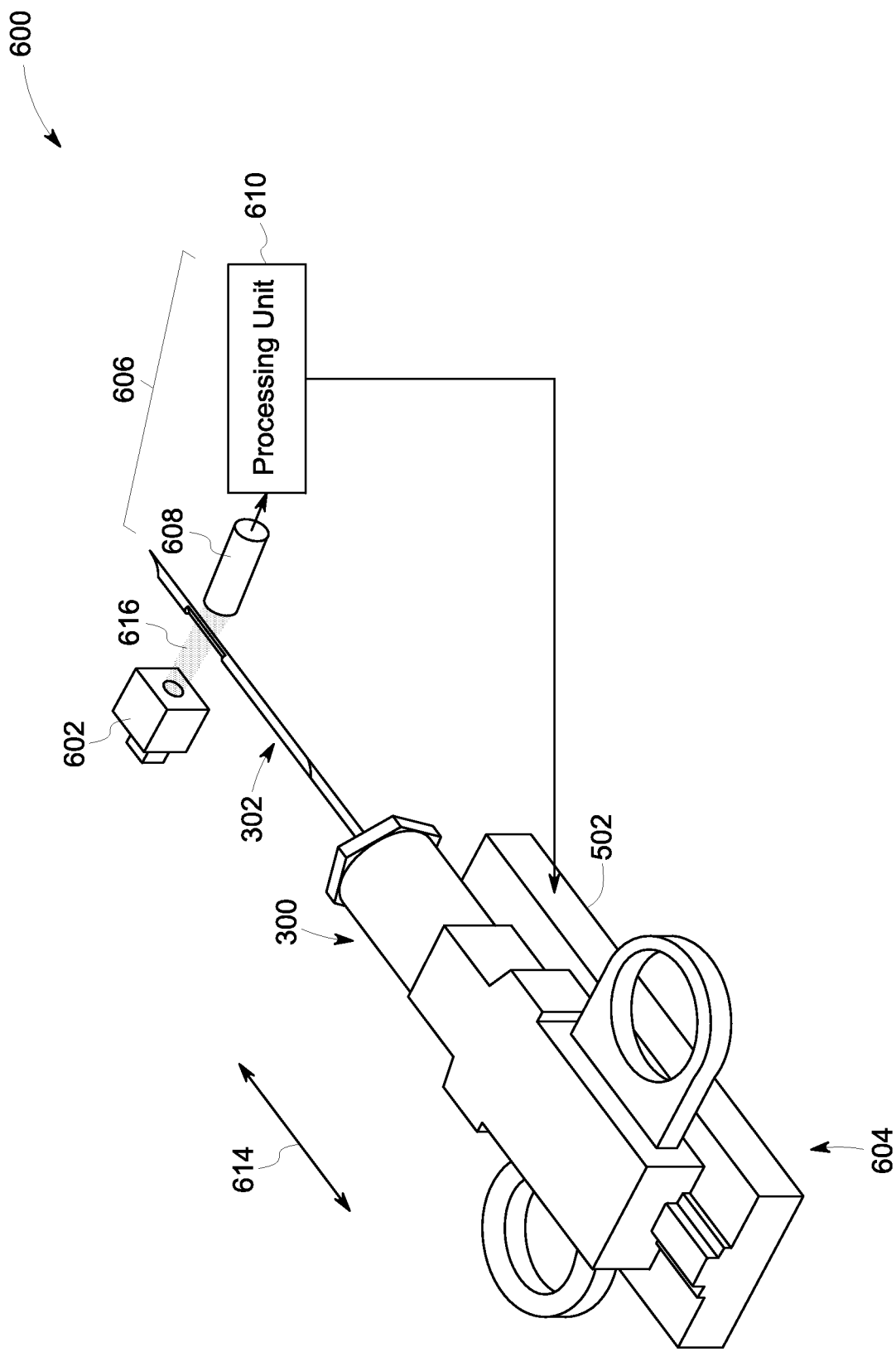
FIG. 6 is a spectroscopy system automatically aligning a biopsy specimen across an illumination light, in accordance with aspects of the present disclosure.

Referring to FIG. 6, a spectroscopy system automatically aligning a biopsy specimen across an illumination light, in accordance with aspects of the present disclosure, is depicted. For ease of understanding of the present disclosure, the spectroscopy system 600 is described with reference to the components of FIGS. 1-5. Reference numeral 602 may be representative of the illumination subsystem 102, reference numeral 604 may be representative of the fixation subsystem 104, and reference numeral 606 may be representative of the detection subsystem 106 of FIG. 1. The illumination sub-system 602 may include a light source 108 that is configured to emit an illumination light and a guiding unit 110 to guide the emitted illumination light towards the detection sub-system 606, as depicted in FIG. 6. In a similar manner, the detection sub-system 606 may be used for receiving the illumination light and processing it to determine the diagnostic tissue in the biopsy specimen. As such the sub-system further comprises a detecting unit 608 and a processing unit 610.

In a presently contemplated configuration, the fixation sub-system 604 includes an attaching unit 502 that is used to hold a biopsy collecting device 300 having the biopsy specimen. Furthermore, the attaching unit 502 that is configured to position the biopsy collecting device 300 at a predetermined position in the spectroscopy system 600. In one example, the attaching unit 502 may include one or more actuators that may receive control signals from the detection subsystem 606 and accordingly move the biopsy collecting device 300 in a forward or backward direction 614 relative to an illumination path 616.

In an exemplary embodiment, the biopsy specimen is automatically aligned to a predetermined position in the spectroscopy system 600. Particularly, a portion of a needle unit 302 of the biopsy collecting device 300 is first placed between the illumination subsystem 602 and the detection subsystem 606. Further, the illumination light that is passing through or above the needle unit 302 is processed by the detection subsystem 606 to determine a current position of the needle unit 302. In one example, if the illumination light is hitting a metal portion, such as a stylet 206 or a cannula 204 of the needle unit 302, the illumination light may not be received by the detection subsystem 606. Thus, there will be a substantial amount of signal drop or the signal may not be received by the detection subsystem 606. In another example, if the illumination light is passing through air above the needle unit 302, the illumination light may not undergo attenuation or transmission losses, and thus, there will be no signal drop at the detection subsystem 606. Based on the signal strength and/or the transmission losses in the received signal, the detection subsystem 606 may determine the current position of the needle unit 302.

Upon determining the current position of the needle unit 302, the detection subsystem 606 may send one or more control signals to the attaching unit 502 to progressively move the needle unit 302 in a forward or backward direction 614 until the biopsy specimen is placed at the predetermined position across the illumination path 616. In one example, if a tip of the needle unit 302, particularly the tip of the stylet 206 is in the illumination path 616, the processing unit 610 may send one or more controls signals to the attaching unit 502 to move the biopsy collecting device 300 in a forward direction relative to the illumination path 616. These control signals are provided to the attaching unit 502 until the biopsy specimen in the collection area of the stylet 206 is placed across the illumination path 616. In one embodiment, the attaching unit 114 may be at a fixed position, and the spectroscopy system including the illumination subsystem 102 and the detection subsystem 106 is adjusted to align the position of the needle unit 302 across the illumination path 616. In another embodiment, the spectroscopy system may be adjusted relative to the movement of the attaching unit 114 to align the position of the needle unit 302 across the illumination path 616.

After placing or positioning the biopsy specimen across the illumination path 616, the illumination light may interact with the biopsy specimen and it may interact with or be attenuated by molecules or chromophores in the biopsy specimen. The resulting re-emitted or attenuated illumination light may be further received by a detecting unit 608 of the detection subsystem 606. In one embodiment, the needle unit 302 may be moved in a forward or backward direction 614 so as to pass the illumination light through multiple locations of the tissue sample in the biopsy specimen. This in turn helps in obtaining a detected signal resulting from illumination lights that passed through one or more locations of the tissue sample.

Furthermore, the detecting unit 608 may receive a light comprising the attenuated illumination light and/or the re-emitted light, and generates an electrical signal corresponding to the received light. Thereafter, the electrical signal corresponding to the received light is sent to the processing unit 610. Further, the processing unit 610 may analyze the generated electrical signal to characterize tissue in the biopsy specimen. More specifically, the electrical signal may be processed by using one or more algorithms to determine one or more parameters of the biopsy specimen. The parameters may include, but not limited to, classification, quantity, quality, adequacy, or other characteristics of diagnostic tissue in the biopsy specimen. The aspect of processing the signal is explained in greater detail with reference to FIG. 7.

Figure 7:
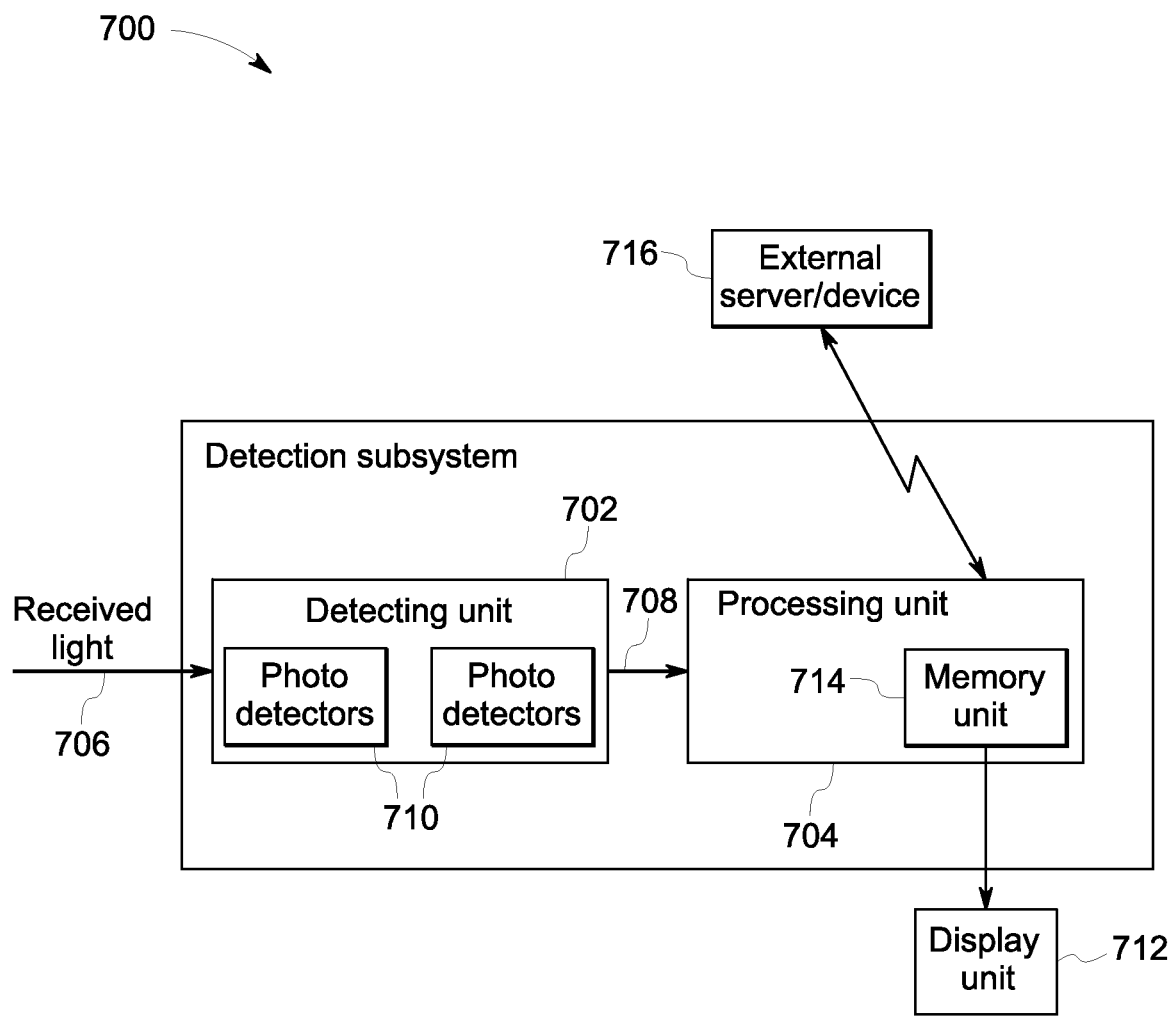
FIG. 7 is a detection subsystem processing a received light to determine the diagnostic tissue, in accordance with aspects of the present disclosure.

Referring to FIG. 7, a detection subsystem processing a received light 706 to determine the diagnostic tissue, in accordance with aspects of the present disclosure, is depicted. The received light 706 may comprise an attenuated illumination light and/or a re-emitted light from the biopsy specimen. Reference numeral 700 may be representative of the detection subsystem 106 of FIG. 1. The detection subsystem 700 includes a detecting unit 702, a processing unit 704, and a display unit 712. The detecting unit 702 may be similar to the detecting unit 116, the processing unit 704 may be similar to the processing unit 118, and the display unit 712 may be similar to the display unit 120 of FIG. 1.

In a presently contemplated configuration, the detecting unit 702 may be aligned with an illumination subsystem 102 to receive the illumination light emitted from the illumination subsystem 102 and the re-emitted light. The illumination light may pass through a biopsy specimen that is positioned between the illumination subsystem 102 and the detection subsystem 106, 700. Particularly, the illumination light may pass through at least one location of a tissue sample of the biopsy specimen. Also, the illumination light may be attenuated while passing through the tissue sample. In one example, the illumination light may be attenuated when molecules or chromophores in the tissue may absorb or scatter the illumination light. The chromophores may include for example, oxy hemoglobin, deoxy hemoglobin, water, DNA, NAD(P)H, FAD, Beta carotene, fat, lipids, collagen, elastin, flavins, or combinations thereof.

As greatly appreciated, the illumination light may interact with the tissue sample in the biopsy specimen and may convey information on the state of the diagnostic tissue. Also, these interactions may yield information for diagnosis at the biochemical, structural, or physiological level of the tissue. In addition, endogenous or exogenous chromophores in the tissue sample may be used for interrogation. The endogenous chromophores such as oxy and de-oxy hemoglobin are known to absorb the illumination light 706 in the wavelength region of about 400 nm to about 700 nm. In this region, tissue scattering is known to dominate over absorption. Additionally, in the UV and near-UV range of the illumination light 706, chromophores such as NAD(P)H, flavins, may provide diagnostic information. Each tissue is known to contain certain chromophores predominantly, and hence analyzing them may convey the absorption characteristics of the tissue.

Furthermore, the detecting unit 702 may include one or more photo detectors 710 that are used for converting the received light 706 to a corresponding electrical signal 708. The electrical signal 708 may represent spectrum of the received light 706. Since the illumination light is attenuated by the biopsy specimen, the spectrum of the received light 706 may include one or more spectra associated with chromophores present in the biopsy specimen. In one example, a tissue sample in the biopsy specimen may contain a mixture of certain chromophores and each chromophore may absorb a particular spectral range of the illuminated light. Further, the converted electrical signal 708 is transmitted to the processing unit 704 that is communicatively coupled to the detecting unit 702.

In the exemplary embodiment, the processing unit 704 may process the electrical signal 708 to verify whether the received light 706 includes a predetermined amount of the attenuated illumination light and/or the re-emitted light. In one example, the processing unit 704 may compare the electrical signal 708 associated with the received light 706 with a threshold value. If the electrical signal 708 is above the threshold value, the processing unit 704 confirms that the received light 706 includes the predetermined amount of the attenuated illumination light and/or the re-emitted light. If the electrical signal 708 is below the threshold value, the processing unit 704 may not further process the signal. In one example, the processing unit 704 may discard the electrical signal 708.

Upon confirming that the received light 706 includes the predetermined amount of the attenuated illumination light and/or the re-emitted light, the processing unit 704 may determine whether a spectrum of the received signal 708 is within a predetermined range. Particularly, a memory unit 714 that is coupled or positioned within the processing unit 704 may be configured to store data having a plurality of library spectra associated with chromophores includes in one or more pre-identified tissue samples. Further, the processing unit 704 may compare the spectrum of the received signal 708 with the plurality of library spectra associated with the chromophores to determine whether the spectrum of the received signal 708 is within the predetermined range.

Further, if the spectrum of the received signal 708 is within the predetermined range, the processing unit 704 may process the received signal 708. Particularly, the processing unit 704 may decompose the received signal 708 into one or more components or constituents of the tissue in the tissue sample. In one embodiment, a known model, such as a physiological model may be used to decompose the signal 708 into one or more components. Particularly, the processing unit 704 may determine a feature for each of the chromophores in the particular location of the tissue sample. Further, the processing unit 704 may develop the physiological model that aids in decomposing the determined feature into the plurality of components. In another embodiment, the signal 708 may be decomposed into principal components through various known methods of principal component analysis (PCA).

After decomposing the signal 708 into one or more components, the processing unit 704 may evaluate the components of the signal 708 to classify the tissue at a particular location in the tissue sample. This location in the tissue sample may be a location from which the attenuated and/or reemitted light 706 is received. In one embodiment, the processing unit 704 may evaluate the components of the signal 708 using a machine learned model. Particularly, in the machine learned model, the processing unit 704 may be first trained with known data-sets, where each of the data-sets represents the type or subtype of the tissues to be classified. In one embodiment, the trained data-sets may be stored in the memory unit 714 as library of data. In one example, this data may include the spectra associated with the chromophores, principal components of the data, and/or information or signatures associated with one or more types of tissue samples including normal and/or diseased tissues.

Further, the processing unit 704 may use this trained information to evaluate data associated with the components of the received signal 708. More specifically, the processing unit 704 may evaluate the data to classify the tissue into one or more tissue types. For example, the processing unit 704 may classify the tissue into tumor or normal tissue type. In another embodiment, the processing unit 704 may classify the tissue into one or more subtypes of a particular tissue type. For example, the processing unit 704 may classify the tissue obtained from a kidney region into one of tissue subtypes, such as papillary, chromophobe, or oncocytoma of a cancer tissue type. In another embodiment, the processing unit 704 may be communicatively coupled to one or more external devices/servers 716 to communicate the classified data to the external devices/servers 716. Further, these external devices/servers 716 may update the known data sets in the memory unit 714 of each of the spectroscopy devices through their corresponding processing unit 704.

In a similar manner, the processing unit 704 may receive light 706 from multiple locations of the tissue sample, and may classify the tissue at a corresponding location into one or more tissue types and/or tissue subtypes. Also, the processing unit 704 may classify the tissue sample into one or more classes based on the classified tissue types at multiple locations of the tissue sample. For example, if the number of classified tumor tissue type is above a threshold number, then the processing unit 704 may classify the overall tissue sample as an adequate tumor tissue sample.

Also, the processing unit 704 may display data associated with the classified tissue types into one or more forms on the display unit 712 for clinical interpretation. In one example, the processing unit 704 may convert the data associated with the classified tissue sample into a gray scale or a color scale. Particularly, the processing unit 704 may convert the data into the gray scale in such a way that an intensity of the gray scale indicates one of the tissue types. Similarly, the processing unit may convert the data into the color scale in such a way that hue saturation of the color scale indicates one of the tissue types.

Figure 8:
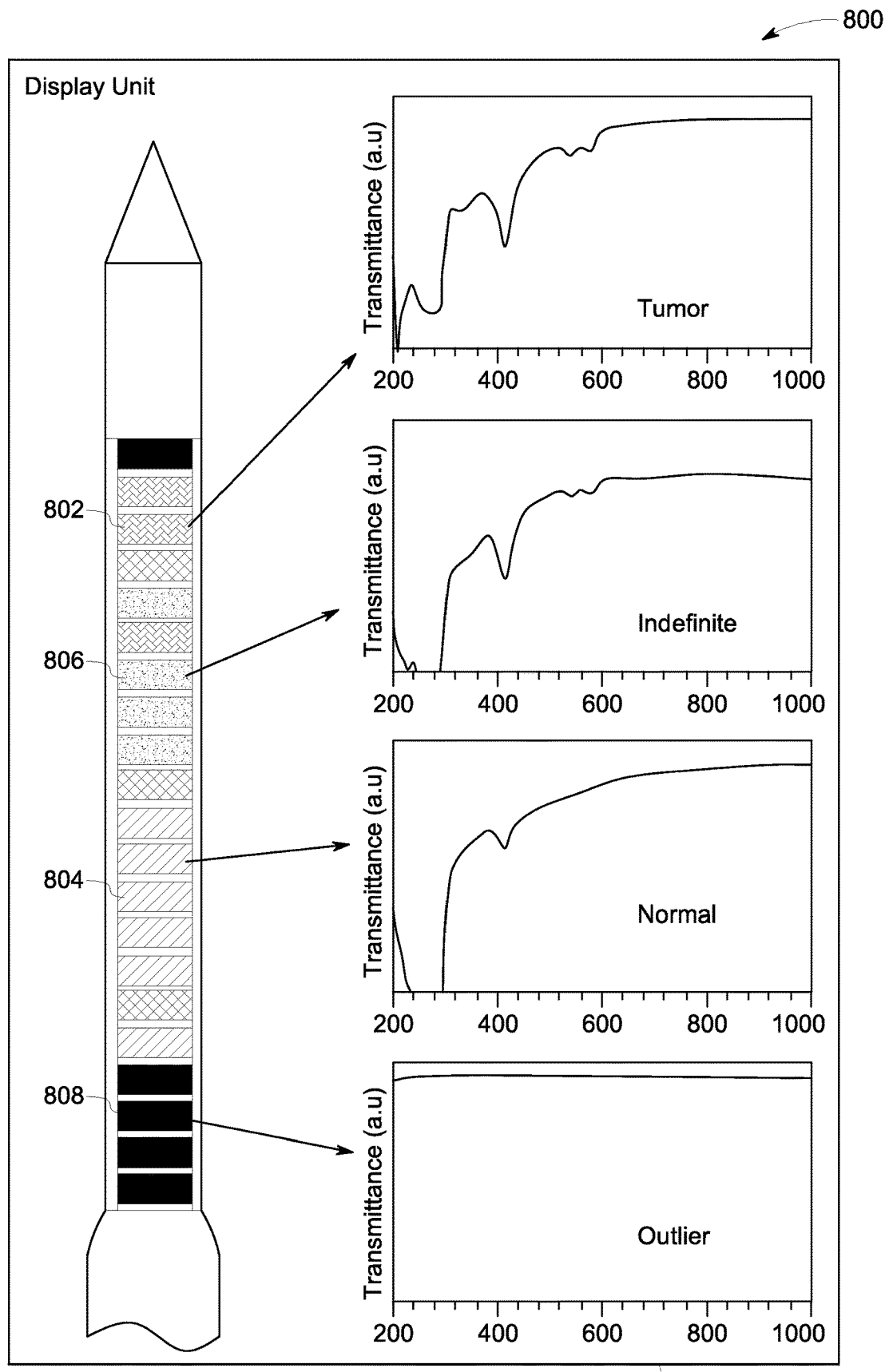
FIG. 8 is a diagrammatical representation of displaying one or more tissue types, in accordance with one embodiment of the present disclosure.

In the embodiment of FIG. 8, the biopsy specimen of a kidney tissue sample is processed to classify the tissue at each location of the tissue sample into one of the tissue types. Particularly, the tissue is classified as tumor or other tissue types and the classified tissue types are displayed on the display unit 712 by different shades of the gray scale, as depicted in FIG. 8. A first shade 802 in the display unit 712 is used to represent that the tissue is a tumor tissue type. A second shade 804 in the display unit 714 is used to represent that the tissue is a normal tissue type, such as fat, blood etc. A third shade 806 in the display unit 716 is used to represent that the tissue is indefinite tissue type. Also, a fourth shade 808 in the display unit 716 is used to represent that the tissue is an outlier of the tissue sample. In addition, FIG. 8 depicts graphs for each tissue type that indicates the transmittance spectra of a corresponding tissue type. In another embodiment, the above mentioned classified tissue types may be represented by different colors of the color scale on the display unit 712.

In one embodiment, the processing unit 704 may indicate the presence or absence of the tumor tissue types with two colors or shades. For example, if the data associated with the tissue is above a threshold value, then the processing unit 704 may indicate the corresponding tissue as a tumor tissue and may display this tissue with a first color or shade on the display unit 712. Otherwise, the processing unit 704 may indicate the tissue as a normal tissue and may display this tissue with a second color or shade on the display unit 712.

In another embodiment, the processing unit 704 may derive a numerical value for the data associated with the classified tissue. Further, the processing unit 704 may display the numerical value adjacent to the assigned color or shades of the classified tissue on the display unit 712.

In yet another embodiment, the processing unit 704 may provide an aggregate recommendation at the biopsy level. Particularly, the processing unit 704 may assign a point for each classified tumor tissue in the tissue sample. If the number of points in the tissue sample is above a threshold number, the processing unit 704 may indicate that the tissue sample is a positive tissue sample on the display unit 704. Otherwise, the processing unit 704 may indicate that the tissue sample is a negative tissue sample on the display unit 704. In this manner, a recommendation of "adequacy" is rendered for each biopsy, given that a minimum amount of tissue is required for adequate downstream molecular testing. This recommendation may be provided with or without immediately revealing the classifier outputs at each location along the tissue sample.

Figure 9:
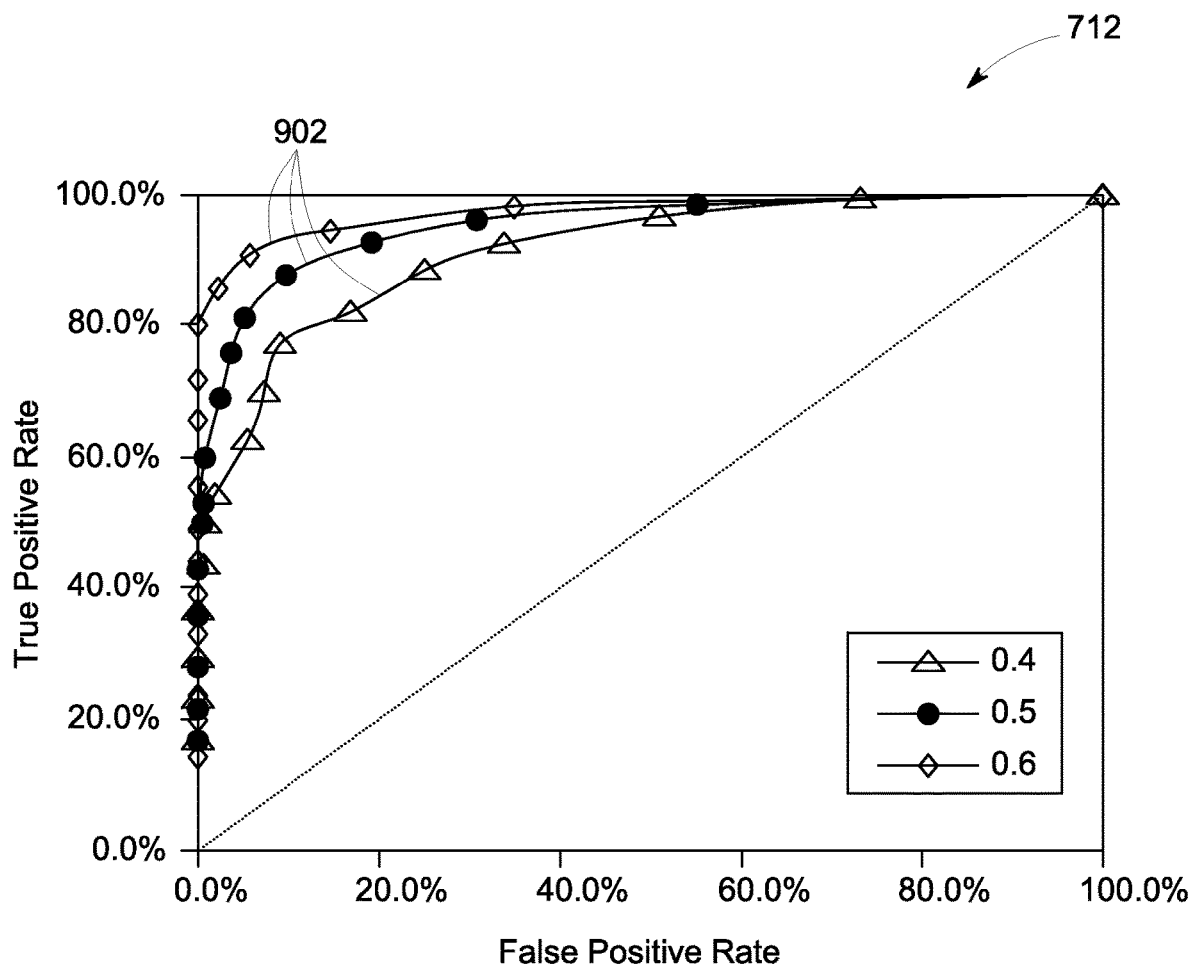
FIG. 9 is a diagrammatical representation of displaying one or more tissue types tissue types, in accordance with another embodiment of the present disclosure.

In one another embodiment, the processing unit 704 may provide a statistical confidence of tissue adequacy for the biopsy. This may be derived from larger sample statistics, such as receiver-operator characteristic curves 902, obtained from relevant academic studies or clinical trials, as depicted in FIG. 9. Particularly, Receiver-operator characteristic (ROC) curve obtained on classification of more than 550 kidney samples are depicted in the display unit 712. Each curve 902 represents the statistical probability used as a cutoff by the classifier. However, in the embodiment of FIG. 9, the ROC curves 902 are performed at the biopsy level, rather than at the individual spectral level.

Furthermore, in one embodiment, the processing unit 704 may also display data associated with the amount of the attenuated illumination light and/or the re-emitted light received from the biopsy specimen. This data may be displayed in one or more forms on the display unit 712. In one example, the processing unit 704 may display this data similar to the data shown in FIG. 8. Particularly, if the data is above the threshold value, the processing unit 704 may assign a first shade or color to the data associated with the received light 706. Otherwise, the processing unit 704 may assign a second shade or color to the data. This information on the display unit 712 would be useful for the user or operator to visually analyze the received light.

In a similar manner, the processing unit 704 may also display the spectrum of the received signal 708 on the display unit 712. In one embodiment, the processing unit 704 may compare the spectrum of the received signal 708 with the plurality of library spectra associated with the chromophores to determine whether the spectrum of the received signal 708 is within the predetermined range. Also, the data associated with the spectrum of the received signal 708 is displayed in one or more forms on the display unit 712. For example, if the spectrum of the received signal 708 is within the predetermined range, the processing unit 704 may assign a first shade or color to the data. Otherwise, the processing unit 704 may assign a second shade or color to the data. It may be noted that the processing unit 704 may display the data associated with the spectrum of the received signal 708 in one or more forms, and is not limited to the color or shade display form as described above.

Figure 10:
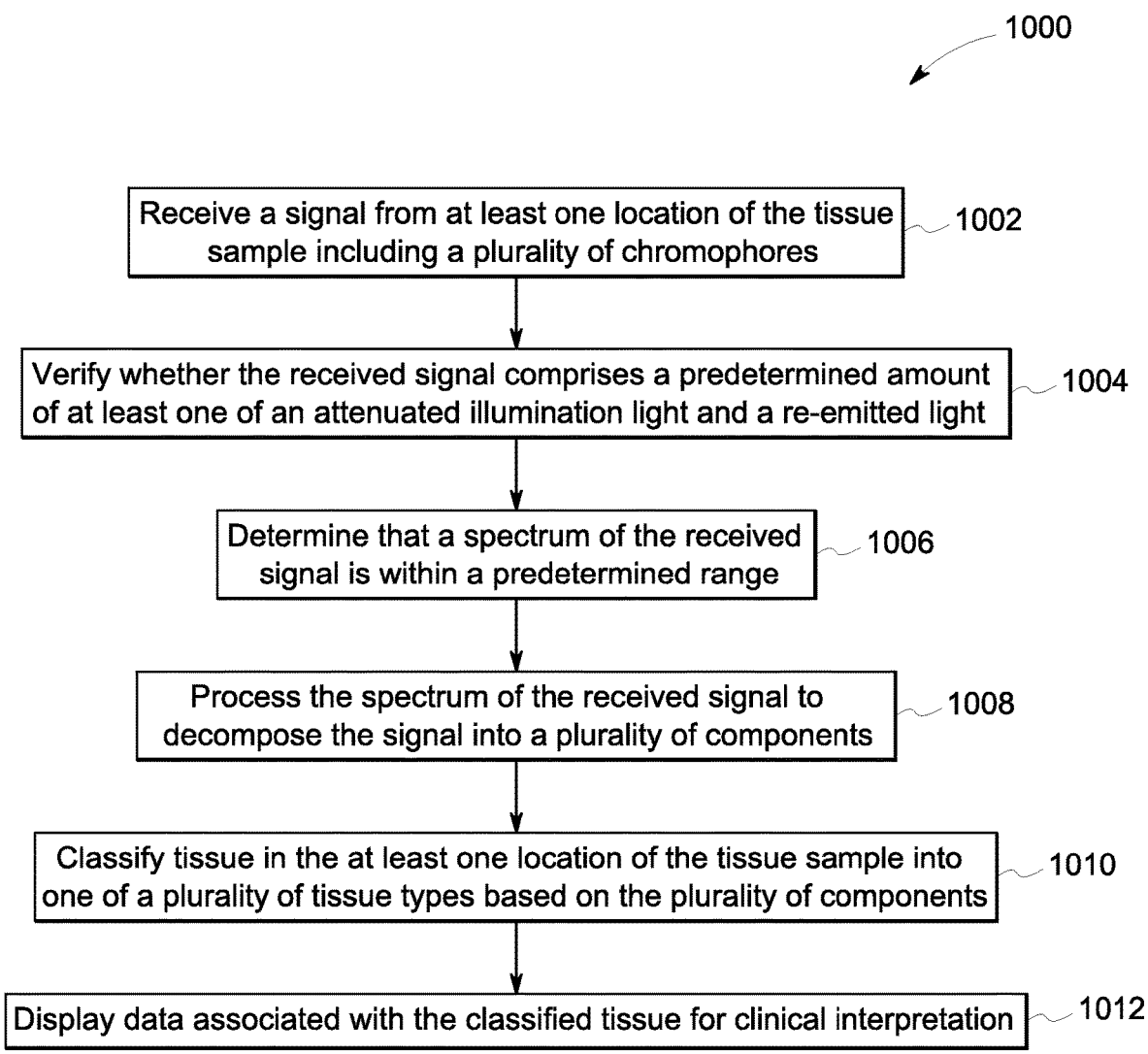
FIG. 10 is a flow chart illustrating a method for classifying tissues in a biopsy specimen, in accordance with aspects of the present disclosure.

Referring to FIG. 10, a flow chart illustrating a method 1000 for classifying a tissue sample of a biopsy specimen, in accordance with aspects of the present disclosure, is depicted. For ease of understanding, the method is described with reference to FIGS. 1-7. The method begins at step 1002, where an illumination light that is passed through at least one location of the tissue sample of the biopsy specimen is received by a detection subsystem 700. To that end, a detecting unit 702 in the detection subsystem 700 is used to receive the light 706 that has interacted with the tissue sample. Particularly, the detecting unit 702 may include one or more photo detectors 710 that are used for converting the received light 706 to a corresponding electrical signal 708. Further, the electrical signal 708 may include a spectrum of the received light. Thereafter, the converted electrical signal 708 is transmitted to the processing unit 704 that is communicatively coupled to the detecting unit 702.

Subsequently, at step 1004, the received signal 708 may be verified to determine whether the signal 708 may include a predetermined amount of at least one of an attenuated illumination light and a re-emitted light. To that end, the processing unit 704 may compare the received light 706 with a threshold value to determine whether the received signal 708 includes the predetermined amount of the attenuated illumination light and/or the re-emitted light.

Furthermore, at step 1006, the spectrum of the received signal 708 is processed by the processing unit 704 to determine that the spectrum of the received signal 708 is within a predetermined range. Particularly, the memory unit 714 may store data having a plurality of library spectra associated with chromophores included in one or more pre-identified tissue samples. Further, the processing unit 704 may compare the spectrum of the received signal 708 with this plurality of library spectra associated with the chromophores to determine whether the spectrum of the received signal 708 is within the predetermined range.

In addition, at step 1008, the spectrum of the received signal is processed by the processing unit 704 to decompose the signal into a plurality of components. In one embodiment, the processing unit 704 may determine a feature for each of the chromophores in the particular location of the tissue sample. Further, the processing unit 704 may develop a physiological model to decompose the determined feature into one or more components.

Further, at step 1010, the tissue at the particular location of the tissue sample is classified into one of a plurality of tissue types based on the plurality of components. In one embodiment, the processing unit 704 may evaluate the components of the signal 708 using a machine learned model. Particularly, in the machine learned model, the processing unit 704 may be first trained with known data-sets, where each of the data-sets represents the type or subtype of the tissues to be classified. Further, the processing unit 704 may use this trained information to evaluate data associated with the components of the received signal 708. More specifically, the processing unit 704 may evaluate the data to classify the tissue into one or more tissue types. For example, the processing unit 704 may classify the tissue into tumor or normal tissue type.

Also, at step 1012, the processing unit 704 may display data associated with the classified tissue for clinical interpretation. To that end, the processing unit 704 may display the data in one or more forms on the display unit 712. This displayed data may aid in evaluation of biopsy adequacy and also for determining different tissue types in the biopsy.

Figure 11:
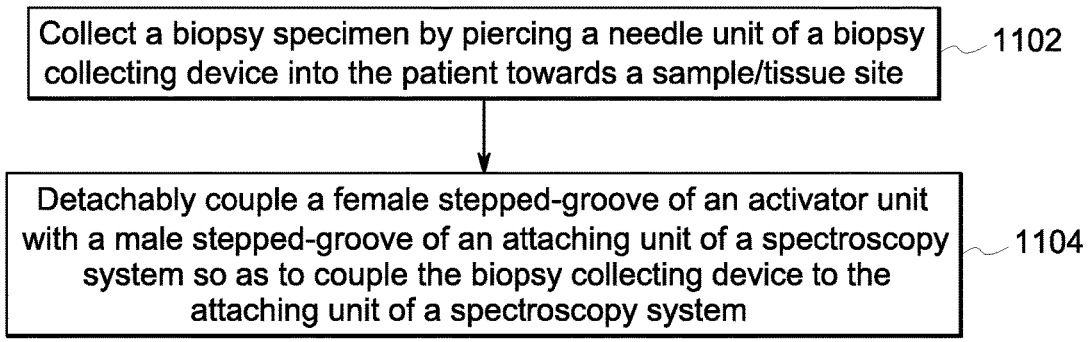
FIG. 11 is a flow chart illustrating a method for holding a biopsy collecting device, in accordance with aspects of the present disclosure.

Referring to FIG. 11, a flow chart illustrating a method 1100 for coupling a biopsy collecting device to a spectroscopy system, in accordance with aspects of the present disclosure, is depicted. For ease of understanding of the present disclosure, the method is described with reference to the components of FIGS. 1-7. The method begins at step 1102, where a biopsy specimen is collected from a patient. Particularly, a needle unit 200 of the biopsy collecting device 300 may be pierced into the patient to collect the biopsy specimen from a desired tissue site in the patient.

Subsequently, at step 1104, the biopsy collecting device 300 is detachably coupled to the spectroscopy system 100. Particularly, the activator unit 304 includes a channel 306 at a bottom surface 308 of the activator unit 304. This channel 306 may be formed with a female stepped-groove 310 along the length of the activator unit 304. Further, the biopsy collecting device 300 is positioned on the attaching unit 502 in such a way that the female stepped-groove 310 mates or couples with the male stepped-groove 504 of the attaching unit 502. Also, the female stepped-groove 310 may be coupled to the male stepped-groove of the attaching unit 502 to form a track area for the biopsy collecting device 300 to move laterally on the spectroscopy system 100.

The various embodiments of the system and method aid in diagnosing tissue in a biopsy specimen. Also, the amount of diagnostic tissue in an excised biopsy specimen is determined without removing the biopsy specimen from a biopsy needle or a biopsy collecting device. This in turn may reduce the time and cost for examining biopsy of a patient. In addition, exposing the biopsy specimen to air may quickly degrade the tissue sample. Therefore, a fast scan of the biopsy specimen directly in the biopsy needle allows for rapid characterization with minimal impact on the biopsy specimen. Also, characterization in the biopsy needle minimizes the impact on existing clinical workflow. Moreover, the diagnostic tissue in the biopsy specimen may be classified into a normal tissue or an abnormal tissue, which in turn aids in determining the quality, the quantity, and other characteristics of the diagnostic tissue in the biopsy specimen.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A biopsy collecting device comprising:
a needle unit configured to extract and receive a biopsy specimen and comprising a cannula and a stylet, the needle unit defining an opening configured to expose the extracted biopsy specimen, wherein the stylet is configured to move relative to the cannula along an axis of the needle unit; and
an activator unit coupled to an end of the needle unit and comprising:
a bottom surface; and
a channel formed in the bottom surface of the activator unit and comprising a female stepped-groove, the channel configured to detachably couple the biopsy collecting device to an attaching unit of a spectroscopy system, the spectroscopy system comprising:
an illumination light configured to emit light to scan the biopsy specimen; and
a detecting unit configured to receive the emitted light that passes through the opening, the detecting unit disposed such that the illumination light and the detecting unit are aligned on a first axis;
wherein the attaching unit is configured to move along the female stepped-groove to move the needle unit along a second axis formed by the cannula of the needle unit to align the opening such that the opening configured to expose the biopsy specimen is disposed between the illumination light and the detecting unit to permit scanning multiple locations within the opening across an illumination light path of the light emitted from the illumination light.

2. The biopsy collecting device of claim 1, wherein the female stepped-groove on the bottom surface of the activator unit engages with a male stepped-groove of the attaching unit.

3. The biopsy collecting device of claim 2, wherein the female stepped-groove is slidably coupled to the male stepped-groove of the spectroscopy system to allow lateral movement of the biopsy collecting device on the attaching unit along the second axis.

4. The biopsy collecting device of claim 1, wherein the attaching unit is configured to slide relative to the activator unit in one of forward and backward directions along the channel.

5. The biopsy collecting device of claim 1, wherein, in a first configuration of the needle unit, the stylet extends from the cannula to align the opening with the illumination path and wherein in a second configuration of the needle unit, the stylet is retracted within the cannula.

6. The biopsy collecting device of claim 5, wherein the opening is covered by the cannula in the second configuration.

7. A method for holding a biopsy collecting device, the method comprising:
extracting and collecting, by a needle unit of the biopsy collecting device, a biopsy specimen from a patient, the needle unit defining an opening configured to expose the biopsy specimen;
detachably coupling a female stepped-groove of an activator unit of the biopsy collecting device with a male stepped-groove of an attaching unit of a spectroscopy system so as to couple the biopsy collecting device to the attaching unit of the spectroscopy system;
moving the attaching unit along the female stepped-groove, wherein the moving moves the needle unit along a first axis formed by a cannula of the needle unit to align the needle unit opening with the exposed biopsy specimen such that the needle unit opening and the exposed biopsy specimen are disposed between an illumination light and a detecting unit configured to receive light emitted from the illumination light and that passes through the opening, the detecting unit disposed such that the illumination light and the detecting unit are aligned on a second axis that passes through the aligned needle unit opening to permit scanning across an illumination light path of the spectroscopy system so that the illumination light of the spectroscopy system scans multiple locations of the biopsy specimen.

8. The method of claim 7, wherein detachably coupling the female stepped-groove of the activator unit comprises snapping the female stepped-groove on the male stepped-groove of the spectroscopy system so as to allow lateral movement of the biopsy collecting device on the attaching unit.

9. The method of claim 8, wherein snapping the female stepped-groove on the male stepped-groove comprises sliding the biopsy collecting device over the attaching unit to align the needle unit opening at a predetermined position in the spectroscopy system to ensure the exposed biopsy specimen is scanned.

10. The method of claim 9, wherein sliding the biopsy collecting device comprises automatically moving the biopsy collecting device over the attaching unit based on a control signal received from the detecting unit.

11. The method of claim 10, wherein automatically moving the biopsy collecting device comprises sliding the activator unit of the biopsy collecting device in one of forward and backward directions based on the received control signal.

12. The method of claim 7, wherein detachably coupling the female stepped-groove comprises attaching the female stepped-groove to the male stepped-groove to form a track area for lateral movement of the biopsy collecting device.

* * * * *